United States Patent [19]

Papenfuhs

[11] Patent Number: 5,744,644
[45] Date of Patent: Apr. 28, 1998

[54] CONCENTRATED SOLUTIONS OF POLYHYDROXYALKYLAMINES AND THEIR USE

[75] Inventor: Bernd Papenfuhs, Neuötting, Germany

[73] Assignee: Hoechst Aktiengesellschaft, Frankfurt, Germany

[21] Appl. No.: 652,148

[22] Filed: May 23, 1996

[30] Foreign Application Priority Data

May 30, 1995 [DE] Germany ............... 195 19 705.4

[51] Int. Cl.$^6$ ................................................. C07C 211/03
[52] U.S. Cl. .............. 564/444; 252/182.24; 252/182.26; 252/182.27; 564/447; 564/473
[58] Field of Search ................... 564/444, 447, 564/473; 252/182.24, 182.26, 182.27

[56] References Cited

U.S. PATENT DOCUMENTS 4,021,539  5/1977  Moller et al. ........................... 424/73

FOREIGN PATENT DOCUMENTS 2349278  4/1975  Germany.
4322874  1/1995  Germany.

*Primary Examiner*—Brian M. Burn
*Attorney, Agent, or Firm*—Connolly and Hutz

[57] ABSTRACT

It has been found that certain polyhydroxyalkylamines have a particularly good solubility in water, alcohols and in mixtures of water and alcohols. The concentrated solutions described consist essentially of water, alcohols, preferably $C_1$–$C_3$-alcohols, or water/alcohol mixtures as solvent and at least one dialkylaminopropylglucamine of the formula 1 below $$Z-NH-CH_2CH_2CH_2-NR^1R^2 \qquad (1)$$

where $R^1$ and $R^2$ are identical or different and are $C_1$–$C_4$-alkyl or hydroxyalkyl having from 2 to 4 carbon atoms and Z is a linear polyhydroxyhydrocarbon radical having at least three OH groups which may, if desired, be alkoxylated. The concentrated solutions are particularly useful for preparing the corresponding polyhydroxyalkylcarboxamides.

4 Claims, No Drawings

CONCENTRATED SOLUTIONS OF POLYHYDROXYALKYLAMINES AND THEIR USE

DESCRIPTION

The invention relates to concentrated solutions of polyhydroxyalkylamines in water, alcohols or in water/alcohol mixtures as solvent and the use of these solutions for preparing polyhydroxyalkylcarboxamides.

Polyhydroxyalkylamines are valuable compounds for the preparation of cosmetics, cf. U.S. Ser. No. 4,021,539. Furthermore, they are advantageous starting compounds for preparing urea derivatives, cf. DE-A-23 49 278, and in particular for preparing the corresponding carboxamides by acylation (amidation) of the amine compound with fatty acid or fatty acid derivatives such as alkyl esters of fatty acids, cf. DE-A-43 22 874. The polyhydroxyalkylamines include, in particular, the amino sugars which in the case of glucose units are referred to as glucamines and in the case of other sugar units are referred to as glycamines. Correspondingly, the resulting carboxamides are referred to as glucamides and glycamides respectively. The compounds in question will hereinafter, merely for the sake of brevity, be referred to as glucamines and glucamides.

Glucamines are prepared by catalytic reductive amination of glucose with amines and are generally marketed as aqueous, alcoholic or aqueous/alcoholic solutions, in particular for preparing the corresponding particularly surface-active glucamides. For the preparation of glucamides, the glucamines are used in the form of a concentrated alcoholic solution and preferably in the form of a glucamine melt, cf. the abovementioned DE-A-43 22 874. Thus, in both cases, more or less concentrated glucamine solutions are desired. Concentrated alcoholic solutions can thus be used as such. If the glucamine compound is to be used in the form of a melt, concentrated solutions require less outlay in terms of equipment and energy for removing the solvent than do dilute solutions. Transport of the solutions likewise results in more or less high costs depending on the concentration of glucamine. Transport in the melt is problematical owing to the lack of thermal stability of glucamines quite generally. As a result, it would be particularly desirable to have glucamines which are readily soluble in water, alcohol or water/alcohol mixtures. Such glucamine compounds would enable the preparation of concentrated solutions, making available a particularly advantageous product for preparing glucamides.

It has surprisingly been found that among the numerous glucamine compounds those selected from the group consisting of dialkylaminopropylglucamines have a particularly high solubility in water, alcohols, in particular $C_1$–$C_3$-alcohols, and in mixtures of water and alcohols.

Accordingly, concentrated aqueous, alcoholic, preferably $C_1$–$C_3$-alcoholic, and aqueous/alcoholic solutions of at least one dialkylaminopropylglucamine of the formula 1 below

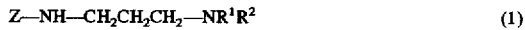  (1)

where $R^1$ and $R^2$ are identical or different and are $C_1$–$C_4$-alkyl or hydroxyalkyl having from 2 to 4 carbon atoms and Z is a linear polyhydroxyhydrocarbon radical having at least three OH groups which may, if desired, be alkoxylated, have been found.

Preference is given to compounds of the formula 1 in which $R^1$ and $R^2$ are methyl and Z is the radical of a sugar alcohol derived from a reducing monosaccharide or disaccharide, in particular from glucose.

Preferred solutions according to the invention consist essentially of a) from 45 to 90% by weight, preferably from 55 to 80% by weight, in particular from 60 to 70% by weight, of at least one compound of the formula 1 and b) from 10 to 55% by weight, preferably from 20 to 45% by weight, in particular from 30 to 40% by weight, of water, of at least one $C_1$–$C_3$-alcohol or of water and at least one $C_1$–$C_3$-alcohol as solvent, percentages by weight being based on the solution.

Preferred $C_1$–$C_3$-alcohols are methanol, ethanol, isopropanol and/or 1,2-propanediol. The volume ratio in the solvent water/alcohol can vary within wide limits. Thus, it is possible to use water/alcohol mixtures which consist predominantly of water or predominantly of alcohol. A preferred volume ratio of the water/alcohol mixtures is from 1:2 to 2:1, with 1:1 being particularly preferred. Among the specified solvents, water and water/alcohol mixtures are preferred.

To the human eye, the solutions according to the invention appear clear and precipitate-free at temperatures above about 15° C. The N,N-dialkyl-N'-polyhydroxyalkylpropylenediamines of the formula 1 proposed according to the invention are thus readily soluble in the specified solvents at room temperature and likewise at higher temperatures. An advantageous temperature range, including for the purposes of transport and storage of the concentrated solutions, is from about 15 to 70° C. The solubility at room temperature is somewhat better in water and in water/alcohol mixtures than in alcohol alone. At higher temperatures, the solubility in all three solvents is virtually equally good. Thus, solutions according to the invention at room temperature consist essentially of, for example, a) from 55 to 70% by weight of at least one compound of the formula 1 and b) from 30 to 45% by weight of water or water/alcohol mixture, percentages by weight being based on the solution. At higher temperatures for example at from 50° to 70° C., highly concentrated solutions are possible, with the solvent also being able to be alcohol alone. Such solutions consist essentially of, for example, a) from 55 to 90% by weight of at least one compound of the formula 1 and b) from 10 to 45% by weight of solvent, percentages by weight being based on the solution.

The preparation of the concentrated glucamine solutions according to the invention is preferably carried out within the framework of the abovementioned reductive amination. Here, sugar compounds corresponding to the radical Z in formula 1 are reductively aminated with an N,N-dialkylalkylenediamine of the formula 2

  (2)

where $R^1$ and $R^2$ are as defined above, in the specified solvents water, alcohol or water and alcohol and in the presence of hydrogenation catalysts to give the glucamine compound of the formula 1. The molar ratio of sugar compound to amine is about 1:1–1.2. The solvent is used in an amount of from about 5 to 50% by weight, based on glucamine compound formed. Preferred solvents are water and the specified water/alcohol mixtures. Catalysts which can be used are the customary hydrogenation catalysts such as palladium on activated carbon, copper chromite and, in particular, Raney nickel in an amount of generally from 0.01 to 3% by weight, preferably from 0.1 to 1% by weight, based on the sugar compound to be aminated. The reductive amination reaction is carried out at a temperature of from 40° to 150° C., preferably from 50° to 120° C., and at a hydrogen pressure of from 10 to 200 bar, preferably from 20 to 100 bar. The catalyst can be removed from the resulting solutions containing the glucamine compound formed by, for example, filtration. Owing to the good solubility of the glucamine in question, dilute reaction solutions can be concentrated, for example simply by evaporation or distillation of the solvent.

The N-(3-dialkylamino)propyl-N-polyhydroxyalkylamines proposed according to the invention have, as already emphasized, an unexpectedly high solubility in the solvents described. Owing to this excellent property in comparison with other glucamines, they are particularly suitable for preparing the corresponding amide compounds. The invention therefore also provides for the use of the described solutions containing the N-functionalized glucamines for preparing polyhydroxyalkylcarboxamides of the formula 3

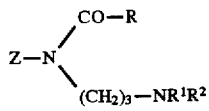

(3)

where R is an aliphatic radical having from 5 to 23 carbon atoms, preferably a fatty alkyl radical having from 7 to 17 carbon atoms, and $R^1$, $R^2$ and Z are as defined above. The preparation of these N-(3-dialkylamino)propyl-N-polyhydroxyalkylcarboxamides, in particular the corresponding glucamides, can be carried out by the process described in the abovementioned publication DE-A-43 22 874. According to this method, the remaining solvent is removed from the concentrated or highly concentrated solutions according to the invention and the glucamine is reacted in the form of a melt with the amidating agent, viz. fatty acid or fatty acid derivative, preferably a $C_1$-$C_4$-alkyl ester of a fatty acid, to form the corresponding N-functionalized glucamide. This preferred reaction using the glucamine compound in the form of a melt is carried out at a temperature of from about 60 to 130° C. and in the presence of an alkaline catalyst. It is described in detail in DE-A-43 22 874, which is incorporated herein by reference.

As regards the polyhydroxyalkyl radical Z in formula 1, the following may also be said: this radical is preferably derived, as already mentioned above, from polyhydroxyalkyl compounds selected from the group consisting of the reducing sugars or reducing sugar derivatives. Preferred reducing sugar compounds are the monosaccharides preferably pentoses and hexoses, and the oligosaccharides, preferably disaccharides and if desired also trisaccharides. Examples of monosaccharides are glucose, galactose, mannose and talose as hexoses and arabinose, ribose and xylose as pentoses. Among the monosaccharides, the hexoses are preferred. Examples of oligosaccharides (polysaccharides) are lactose, maltose, maltotriose and the like. Particularly preferred polyhydroxyalkyl radicals are derived from reducing hexoses, in particular from glucose (sorbityl radical).

The invention will now be illustrated by means of a report on the solubility of various glucamines.

The solubility of N-(3-dimethylamino)propylglucamine of the formula I and of analogous N-substituted glucamines, namely N-methylglucamine, N-butylglucamine and N-hexylglucamine, in water, in a mixture of water and isopropanol in a volume ratio of 1:1 and in methanol was tested. The glucamine compounds to be compared in respect of solubility were taken up in the specified solvents while stirring at 60° C. in concentrations of from 10 to 70% by weight and subsequently stored for 5 days at 60° C. and at room temperature (20° C.). The results of these storage tests are summarized in the table below, in which "+" indicates fluid, storage-stable solutions which appear clear and precipitate-free to the human eye and "–" indicates the formation of turbidity, precipitates or even solidification. Furthermore, "RT" is used as an abbreviation for room temperature and "DMAP-glucamine" is used as an abbreviation for N-dimethylaminopropylglucamine of formula 1. As the table shows, the differences in the solubility are most pronounced in methanol as solvent. In water too, N-butylglucamine and N-hexylglucamine are virtually insoluble and the shorter-chain N-methylglucamine can be dissolved in high concentration only at a relatively high temperature (60° C.). In contrast, the N-dimethylaminopropylglucamine proposed according to the invention is significantly more soluble under all conditions tested, so that the concentrated to highly concentrated solutions described are possible.

TABLE

| | Solubility of the glucamine compounds | | | | | | | |
|---|---|---|---|---|---|---|---|---|
| | N-Methyl-glucamine | | N-Butyl-glucamine | | N-Hexyl-glucamine | | DMAP-glucamine | |
| Concentration in % by weight | RT | 60° C. | RT | 60° C. | RT | 60° C. | RT | 60° C. |
| in water | | | | | | | | |
| 70 | – | + | – | – | – | – | + | + |
| 60 | – | + | – | – | – | – | + | + |
| 50 | – | + | – | – | – | – | + | + |
| 40 | + | + | – | + | – | – | + | + |
| 30 | + | + | – | + | – | – | + | + |
| 20 | + | + | – | + | – | – | + | + |
| 10 | + | + | + | + | – | + | + | + |
| in water/isopropanol (1:1) | | | | | | | | |
| 70 | – | + | – | – | – | – | – | + |
| 60 | – | + | – | – | – | – | + | + |
| 50 | – | + | – | + | – | + | + | + |
| 40 | – | + | – | + | – | + | + | + |
| 30 | + | + | – | + | – | + | + | + |
| 20 | + | + | – | + | – | + | + | + |
| 10 | + | + | + | + | – | + | + | + |
| in methanol | | | | | | | | |
| 70 | – | – | – | – | – | – | – | + |
| 60 | – | – | – | – | – | – | – | + |
| 50 | – | – | – | – | – | – | – | + |
| 40 | – | – | – | – | – | – | + | + |
| 30 | – | – | – | – | – | – | + | + |
| 20 | – | + | – | – | – | – | + | + |
| 10 | – | + | – | + | – | + | + | + |

I claim:

1. A solution which comprises at least one dialkylaminopropylglucamine of the formula 1 below

where $R^1$ and $R^2$ are identical or different and are $C_1$-$C_4$-alkyl or hydroxyalkyl having from 2 to 4 carbon atoms and Z is a linear polyhydroxyhydrocarbon radical having at least 3 OH groups optionally alkoxylated wherein the solvent is water, alcohol, or a water/alcohol mixture, and wherein said solution contains from 45–90% by weight of at least one compound of the formula 1 at a temperature of 15°–70° C.

2. A solution which comprises at least one dialkylaminopropylglucamine of the formula 1 below

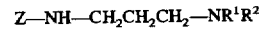

where $R^1$ and $R^2$ are identical or different and are $C_1$-$C_4$-alkyl or hydroxyalkyl having from 2 to 4 carbon atoms and Z is a linear polyhydroxyhydrocarbon radical having at least 3 OH groups optionally alkoxylated wherein the solvent is water and wherein said solution contains from 60–90% by weight of at least one compound of the formula 1 at a temperature of at least 15° C.

3. A solution which comprises at least one diallcylaminopropylglucamine of the formula 1 below

Z—NH—CH$_2$CH$_2$CH$_2$—NR$^1$R$^2$ where R$^1$ and R$^2$ are identical or different and are C$_1$–C$_4$-alkyl or hydroxyalkyl having from 2 to 4 carbon atoms and Z is a linear polyhydroxyhydrocarbon radical having at least 3 OH groups optionally alkoxylated wherein the solvent is a water/alcohol mixture and wherein said solution contains from 40–70% by weight of at least one compound of the formula 1 at a temperature of at least 15° C.

4. A solution which comprises at least one dialkylaminopropylglucamine of the formula 1 below

Z—NH—CH$_2$CH$_2$CH$_2$—NR$^1$R$^2$ where R$^1$ and R$^2$ are identical or different and are C$_1$–C$_4$-alkyl or hydroxyalkyl having from 2 to 4 carbon atoms and Z is a linear polyhydroxyhydrocarbon radical having at least 3 OH groups optionally alkoxylated wherein the solvent is an alcohol and wherein said solution contains from 20–40 % by weight of at least one compound of the formula 1 at a temperature of at least 15° C.

* * * * *